(12) United States Patent
Nishiguchi et al.

(10) Patent No.: US 7,846,727 B2
(45) Date of Patent: Dec. 7, 2010

(54) SUBSTRATUM HAVING A PATTERN OF CELL-CULTURE CONTROLLING SUBSTANCE

(75) Inventors: Kenji Nishiguchi, Kanagawa (JP); Takeshi Miyazaki, Kanagawa (JP); Ryoichi Matsuda, Tokyo (JP); Kohei Watanabe, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 338 days.

(21) Appl. No.: 10/108,470

(22) Filed: Mar. 29, 2002

(65) Prior Publication Data

US 2002/0182721 A1 Dec. 5, 2002

(30) Foreign Application Priority Data

Mar. 29, 2001 (JP) ............... 2001-096993
Mar. 29, 2001 (JP) ............... 2001-097219

(51) Int. Cl.
*C12N 5/07* (2010.01)
*C12N 11/02* (2006.01)
*C12N 5/00* (2006.01)
*C12Q 1/02* (2006.01)
*C12M 1/00* (2006.01)

(52) U.S. Cl. .................. 435/395; 435/29; 435/177; 435/325; 435/283.1

(58) Field of Classification Search ............... 435/174, 435/176, 177, 180, 325, 395
See application file for complete search history.

(56) References Cited

U.S. PATENT DOCUMENTS

| 5,108,926 | A | 4/1992 | Klebe ............... 435/284 |
| 6,103,479 | A * | 8/2000 | Taylor ............... 435/7.2 |
| 6,368,838 | B1 * | 4/2002 | Singhvi et al. ...... 435/177 |

FOREIGN PATENT DOCUMENTS

EP 1248108 A2 10/1992

WO WO 97/45730 A1 12/1997

OTHER PUBLICATIONS

*Protein, Nucleic Acid and Enzyme*, vol. 45, No. 5, pp. 727-734 (2000).
Yoshihiro Ito et al., "Photoimmobilization of Insulin onto Polystyrene Dishes for Protein-Free Cell Culture," 12(5) *Biotechnol. Prog.* 700-702 (1996).
Ji Zheng, et al., "Growth Enhancement of Anchorage-Dependent and Anchorage-Independent Cells by Coimmobilization of Insulin with Poly(allylamine) or Gelatin," Biotechnol. Prog., vol. 11, No. 6, pp. 677-681 (1995).
Robert J. Kiebe, "Cytoscribing: A Method for Micropositioning Cells and the Construction of Two- and Three-Dimensional Synthetic Tissues," Experimental Cell Research, vol. 179, No. 2, pp. 362-373 (1988).
Avri Ben-Ze'ev, et al., "Protein Synthesis Requires Cell-Surface Contact while Nuclear Events Respond to Cell Shape in Anchorage-Dependent Fibroblasts", Cell, vol. 21, Sep. 1980, pp. 365-372.
Judah Folkman, et al., "Role of cell shape in growth control", Nature, vol. 273, Jun. 1, 1978, pp. 345-349.
D. Gospodarowicz, et al., "Determination of Cellular Shape by the Extracellular Matrix and Its Correlation with the Control of Cellular Growth", Cancer Research, vol. 38, Nov. 1978, pp. 4155-4171.
Donald E. Ingber, et al., "Endothelial Growth Factors and Extracellular Matrix Regulate DNA Synthesis Through Modulation of Cell and Nuclear Expansion", In Vitro Cellular & Developmental Biology, vol. 23, No. 5, May 1987, pp. 387-394.
Yoshihiro Ito, et al., "Enhancement of cell growth on growth factor-immobilized polymer film", Biomaterials, vol. 12, Jul. 1991, pp. 449-453.

* cited by examiner

*Primary Examiner*—David M Naff
(74) *Attorney, Agent, or Firm*—Fitzpatrick, Cella, Harper & Scinto

(57) ABSTRACT

The present invention relates to a substrate for cell culture capable of controlling at least one function selected from adhesion, proliferation, differentiation, survival, maintenance of undifferentiated state, and apoptosis of a cell. The substrate comprises an immobilization area of controlling substances involved in at least one of the functions of adhesion, proliferation, differentiation, survival, maintenance of undifferentiated state and apoptosis of cells, for example: and the areas are formed by supplying a liquid containing the controlling substances to the substrate by small microdroplet ejection means and immobilizing the controlling substance on the substrate.

12 Claims, 8 Drawing Sheets

FIG. 1
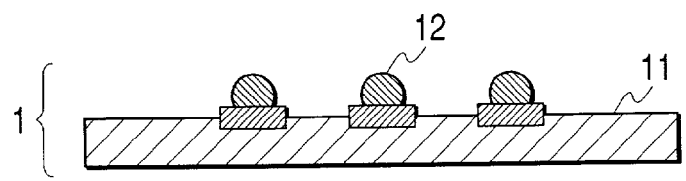
FIG. 2
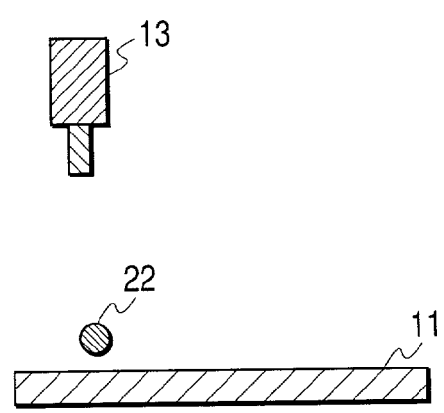
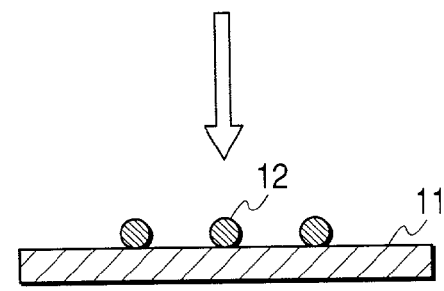
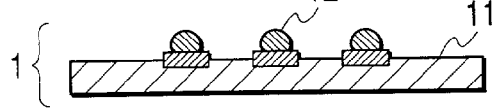

SUBSTRATUM HAVING A PATTERN OF CELL-CULTURE CONTROLLING SUBSTANCE

BACKGROUND OF THE INVENTION

1. Field of the Invention

The present invention relates to substrata to be employed for culturing cells controlling at least one of the cellular functions, i.e., adhesion, proliferation, differentiation, survival, maintenance of undifferentiated state, and apoptosis. The present invention also relates to production methods of the same, cell culture methods and cell culture apparatuses using the same. More particularly, the invention relates to a substratum onto which a substance that affects at least one of the above cellular functions is immobilized by means for ejecting fine droplets, a production method of the same, and a method for cell culture using the same. Also, the invention relates to a method of cell culture controlling cell proliferation or differentiation using a substance that affects at least one of them, as well as to a substratum for cell culture suitable to be used for this method, a production method of the substratum and a cell culture apparatus.

2. Related Background Art

Recently, animal and plant cell cultivation under various conditions or metabolic products thereof are very actively studied, especially, production of substances of which chemical synthesis are impossible or very difficult are investigated in various fields utilizing certain cell activities.

On the other hand, with rapid progress in cell engineering and medical engineering, microbiosensors, artificial organs, and also neuron computers using cells have drawn attentions, and are under active development. The substance that affects a cellular function such as cell adhesion, proliferation, differentiation, survival, maintenance of undifferentiated state and apoptosis may be different depending on individual cells, and in many cases, a plurality of substances affect a certain cellular function in combination. Thus, in order to carry out cell culture while controlling these functions, it is indispensable to specify culture conditions including substances to be used, their combinations and proportions.

U.S. Pat. No. 5,108,926 discloses a cell positioning method to form patterns of cell-adhesion proteins on a substrate with an ink jet printer, and apparatuses for it.

Also, a report (Biotechnol. Prog., 12, 700-702, (1996)) studies effect of cell growth factors that affect cell proliferation and differentiation by immobilizing them on a substrate using photolithography.

Japanese Patent Application Laid-Open No. 2000-512009, discloses a method of cell screening by immobilizing substances that affect cell adhesion properties on a substrate. It teaches that reactive functional groups are introduced onto the substrate and the cell-adhesion substance is immobilized to the substrate via a divalent cross-linking agent. Photolithography was used to bond the functional group and the cell-adhesive substance.

SUMMARY OF THE INVENTION

According to the investigation by the inventors of the present invention, however, the apparatuses and the techniques of the above-described prior arts must be improved, for example, for more efficient cell culture, and use of photolithography is insufficient in view of cost reduction of the above-mentioned controlled cell culture and in order to speed up disease treatment based on it.

Hence, an object of the present invention is to solve the problems of the above-mentioned prior arts. The present invention provides a substratum for cell culture that is produced by simple process and enables cell culture controlling at least one cellular function selected from cell adhesion, proliferation, differentiation, survival, maintenance of undifferentiated state and apoptosis, and a production method thereof. The present invention aims at providing a basic technology for further development of cell engineering and for production of a variety of devices utilizing cells.

Another object of the invention is to provide a cell culture method capable of controlling at least one function selected from adhesion, proliferation, differentiation, survival, maintenance of undifferentiated state and apoptosis.

The invention provides, in one aspect, a substratum for culturing cells provided with an area where a cell-culture controlling substance is immobilized thereon, the substance being involved in at least one function selected from the group consisting of adhesion, proliferation, differentiation, survival, maintenance of undifferentiated state and apoptosis of cells, wherein the area is formed by applying a liquid containing the substance to a base with an apparatus that ejects a liquid in the form of small droplet, and immobilizing the substance to the base.

In another aspect, the invention includes a process for producing a substratum for culturing a cell, comprising the steps of:

(a) applying a liquid containing a cell-culture controlling substance involved in at least one function for adhesion, proliferation, differentiation, survival, maintenance of undifferentiated state and apoptosis of cells with an apparatus the ejects a liquid in the form of droplet to a base; and (b) immobilizing the substance in the liquid applied on the based in the step (i).

In still another aspect, the present invention provides a substratum for culturing cells provided with an area where a cell-culture controlling substance is arranged in a pattern of strip or dot, the substance being involved in at least one function for adhesion, proliferation, differentiation, survival, maintenance of undifferentiated state and apoptosis of cells, wherein the width of the pattern of the area is equal or smaller than that of a cell to be cultured on the substratum.

In still another aspect, the invention includes A process for producing a substratum for culturing cells, the substratum being provided with an area where a cell-culture controlling substance is immobilized thereon, the substance being involved in at least one function selected from the group consisting of adhesion, proliferation, differentiation, survival, maintenance of undifferentiated state and apoptosis of cells, the process comprising a step of: applying the substance to a base so that the area or areas are formed in a pattern of strip, or in dotted pattern, wherein the width of the pattern is equal to or smaller than that of a cell to be cultured on the substratum.

In still another aspect, the invention includes A process for producing a substratum of claim 21 or 22, the process comprising the steps of:

(a) applying the cell-culture controlling substance on a base; and (b) applying a liquid containing cell-nonadhesive substance to the base with an apparatus that ejects the liquid in the form of a droplet so that the pattern is formed.

In still another aspect, the invention provides a process for culturing cells comprising the steps of:

providing the substratum of claim 1, 21 or 22; and culturing cells on the substratum so that culture medium contacts with the area of the substratum.

In still another aspect, the invention provides a substratum provided with areas where a cell-culture controlling substance is immobilized thereon respectively, the substance being involved in at least one function selected from the group consisting of adhesion, proliferation, differentiation, survival, maintenance of undifferentiated state and apoptosis of cells, each of the areas being formed by applying a liquid containing the cell-culture controlling substance with an apparatus that ejects the liquid in the form of a droplet, the areas being spaced out, wherein cells are attached to at least one of the areas.

In still another aspect, the invention provides a substratum for use in controlled cell proliferation or cell differentiation, provided with areas where a cell-culture controlling substance is attached the cell-culture controlling substance being involved in at least one function selected from the group consisting of adhesion, proliferation, differentiation, survival, maintenance of undifferentiated state and apoptosis of cells, the area being formed by applying a liquid containing the cell-culture controlling substance with an apparatus that ejects the liquid in a form of a droplet, so that the area is in a pattern of a strip or in dotted pattern, wherein the width of the pattern is equal to or smaller than that of a cell to be cultured on the substratum.

In another aspect, the invention provides an apparatus for cell culture, comprising a means for culturing cells in a state where the cell culture controlling substance carried with the substratum of claim 1, 21 or 22 is brought into contact with a culture medium.

BRIEF DESCRIPTION OF THE DRAWINGS

FIG. 1 is a cross-sectional view of a cell culture substratum according to a first embodiment of the invention;

FIG. 2 is a process flow chart of one exemplary production method of the substratum according to the first embodiment;

DETAILED DESCRIPTION OF THE INVENTION

Figure 3:
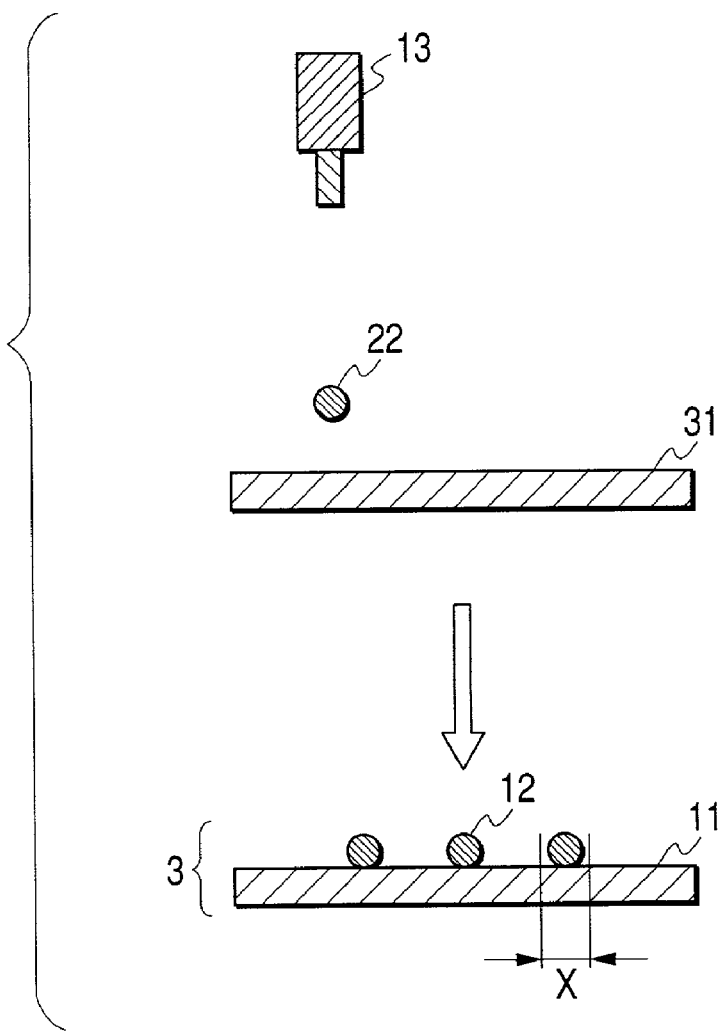
FIG. 3 is a process flow chart of one exemplary production method of a cell culture substratum according to a second embodiment of the invention.

Hereinafter, the invention will be described in detail.

First Embodiment

In a first aspect, the present invention provides a substrate for cell culture having an area where a substance that affects at least one function selected from cell adhesion, proliferation, differentiation, survival, maintenance of undifferentiated state and apoptosis (hereinafter referred to as a controlling substance) is immobilized. The area is formed by applying a liquid containing the controlling substance by microdroplet ejection means.

The substratum for cell culture (hereinafter may be referred to as the substratum) is described with reference to FIG. 1 showing the cross-sectional view of the substratum. The substratum 1 has an immobilization area 12 where the controlling substance is disposed in desired positions and immobilized on a base 11 so that the controlling substance may not escape into the culture fluid to loose the function during cultivation. Being immobilized to the base 11, the controlling substance will not be eluted even when the surface of the substratum comes into contact with the flow of culture medium. Further, as described later, the controlling substance is prevented from being taken by cells during cultivation. Therefore, as described later, the substance stimulates cells constantly. As a result, influence of the controlling substance to the cell culture continues, with advantage such as the improved growth efficiency.

As described above, the controlling substance includes substances affecting at least one function selected from cell adhesion to the substratum 1, cell proliferation (promotion and suppression), differentiation (promotion and suppression), survival, maintenance of undifferentiated state and apoptosis. Examples of such substances include extracellular substrata proteins and antibodies and cytokines that specifically bind to, for example, cell surface, chemical substances that bind to or are taken by the cell to affect the proliferation and differentiation of cell. The examples of the extracellular substrata proteins include collagen, elastin, fibronectin, laminin, and the like. Further, the cytokines include hormones such as insulin and adrenaline and cell growth factors such as nerve growth factor (NGF), epidermal growth factor (EGF), and fibroblast growth factor (FGF).

The controlling substance immobilized in one immobilization area of a substratum may be one than one type. For example, immobilizing two or more types of controlling substances having different functions in one immobilization area enables more advanced control of cellular functions. The controlling substances can be immobilized to a substratum considering their types, chemical and physical properties, and disposition patterns.

The controlling substances immobilized in a plurality of separate immobilization areas need not to be the same, may be different depending to the purpose of the cell culture.

Further, when a plurality of controlling substances are immobilized in one area, the combination of the controlling substances may be the same or different between separate immobilization areas. Even when the combination of the controlling substances is the same between separate immobilization areas, it may be useful to vary concentrations thereof. With such a substratum, cells can be cultured under different conditions to control at least one function selected from adhesion, proliferation, differentiation, survival, maintenance of undifferentiated state and apoptosis. When the probable synergic effect of controlling substances on cell culture is considered, information about the environment that affects the cell culture most may be obtained by changing the combination and concentration of the controlling substances in a plurality of immobilization areas.

Immobilization of the controlling substances on a base 11 may be carried out through the covalent bond, the electrostatic attraction, or affinity. When the controlling substance is immobilized on the base 11 through a covalent bond, it is immobilized by a strong force to form stable immobilization areas on the base and the bonding is hardly affected by the cells and the culture medium.

For example, a method of immobilizing insulin as a controlling substance to a base 11 via a covalent bond is described.

First, a linker, 4-azidobenzoic acid N-hydroxysuccinimide ester, is introduced into insulin as shown by the following equation.

[Formula 1]

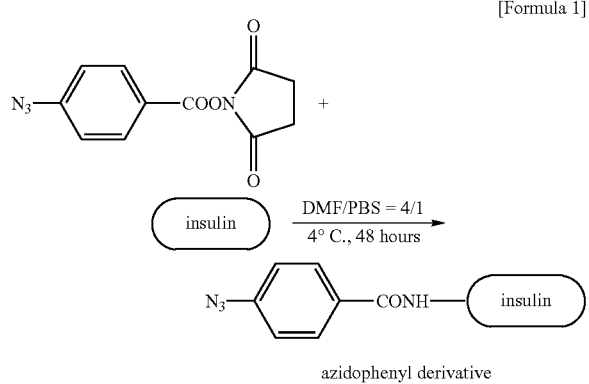

Then the thus obtained solution of the linker-attached insulin is applied to a base such as a polyethylene terephthalate (PET) base, using an ink jet printer. Next, by UV irradiation, the azide group of the linker is cleaved to form an amide bond with a carbon atom of the PET base, so that insulin is covalently bonded to the base surface as shown below.

[Formula 2]

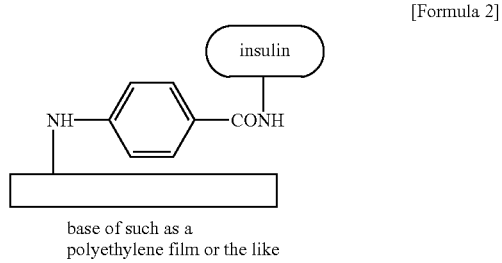

The inventors of the present invention have found that the growth rate of cells cultured with a substratum on which insulin is immobilized is much higher than that of the cells cultured in a culture medium containing insulin in a dissolved state. The reason is not clear yet, but is considered that when insulin is immobilized on a base, insulin is hardly consumed by cells and cells are continuously stimulated by the insulin, whereas when insulin is dissolved in the medium, it is taken by cells and consumed.

When insulin is immobilized by electrostatic attraction, the immobilization areas can be formed on the base 11 without chemical treatment so that possible modification of the controlling substance due to the chemical treatment can be avoided. Further, when the immobilization areas are formed on the base 11 utilizing biological affinity, the immobilization treatment of the controlling substance is relatively easy enabling stable immobilization.

The material and the shape of the base 11 may be optional as long as the base can immobilize the controlling substances stably on it. Practically, a glass substrate, a plastic plate, a plastic sheet, a polymer film, paper and the like are preferable to be used. Further, the base 11 may be transparent, light-shielding or colored. Further, in order to immobilize the controlling substances on the base 11 or to increase the stability of the controlling substance on the base 11, a part of or entire surface of the base 11 may be treated chemically or with radiation.

Further, in the base 11, the area 12 in which the controlling substance is immobilized may be formed singly or in plurality in a sunken part formed on the base surface. This allows easy application of droplets by microdroplet ejection means to prescribed positions of the substrate, and further it allows to culture cells using different culture fluids in respective wells.

Alternatively, the area 12 singly or in plural may be surrounded by a wall-like structure. This allows easy application of droplets by microdroplet ejection means to prescribed positions of the substratum, and further it allows to culture cells using different culture fluids in respective wells. Additionally, such a wall-like structure on the base 11 can be made by photolithography, which enables easy construction of fine wall-like structure. Here, employment of the photolithography is to form the wall-like structure and would not lead to any consumption of controlling substances.

Next, a production method of the cell culture substratum 1 of the above-described constitution is described practically, referring to FIG. 2. At first, if necessary, a base 11 may be subjected to the above-described pretreatment. Practically, the base 11 may be washed to remove undesired substances or it may be subjected to various chemical or physical treatments such as radiation exposure including UV irradiation, corona discharge and the like. Also, if necessary, a polymer material or a silane coupling agent may be applied to the entire or part of surface of the base 11.

Then the controlling substance is positioned on the base 11. For positioning, for example, droplet ejecting means 13 may be employed. The microdroplet ejection means ejects droplets of very small volume, e.g., 100 pl or less, more practically, about 2 to 4 pl, including micropipets, microdispensers, and ink-jet apparatuses. In view of easy preparation, cost and controlled precise ejection of small droplets, the ink-jet system is preferable, and especially the thermal ink jet method and the piezoelectric ink jet method are preferable. The ejection apparatus by the thermal ink jet system has advantages that the minute processing of the ejection orifice is easy, and it can eject liquid to prescribed positions in a high density, so that the controlling substance can be located on the substratum precisely. On the other hand, in the ejection apparatus deformation of a piezoelectric element generates ejection energy, so that the liquid containing the controlling substance 12 is ejected stably without thermal stress.

The controlling substance is dissolved or dispersed in a proper solvent for ejection. For this purpose, any solvent or dispersion medium may be employed as long as it can stably dissolve or disperse the controlling substance, but water is preferable to be used. It is preferable to use ion exchanged water (deionized water) and various buffer solutions to stably dissolve the controlling substance 12.

Further, if necessary, a water-soluble solvent may be used. Any water-soluble solvent is usable as long as it dissolves in water, for examples, alkyl alcohols of 1 to 4 carbons such as methyl alcohol, ethyl alcohol, n-propyl alcohol, isopropyl alcohol, n-butyl alcohol, sec-butyl alcohol and tert-butyl alcohol; amides such as dimethylamide and dimethylacetamide; ketones or ketoalcohols such as acetone and diacetone; ethers such as tetrahydrofuran and dioxane; polyalkylene glycols such as polyethylene glycol and polypropylene glycol; alkylene glycols containing an alkylene group of 2 to 6 carbons such as ethylene glycol, propylene glycol, butylene glycol, triethylene glycol, 1,2,6-hexanetriol, thiodiglycol, hexylene glycol and diethylene glycol; glycerin; lower alkyl ethers of polyhydric alcohols such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether and triethylene glycol butyl ether; N-methyl-2-pyrrolidone; 2-pyrrolidone; 1,3-dimethyl-2-imidazoline and the like. Among a large number of these water-soluble organic solvents, polyhydric alcohols such as diethylene glycol and lower alkyl ethers such as triethylene glycol monomethyl ether are preferable.

In case of the thermal jet type, addition of a lower alkyl ether of ethanol, isopropyl alcohol, or a polyhydric alcohol is preferable since it allows stable bubble formation of the liquid on the film resistor member in the ejection head.

In addition, the liquid containing the substance 12 according to the invention may contain a surfactant, a defoaming agent, an antiseptic, an inorganic or organic salt and the like according to necessity to confer the liquid desired physical properties.

Any surfactant may be used as long as it does not have adverse effect on storage stability of the controlling substance 12, for example, anionic surfactants such as fatty acid salts, higher alcohol sulfuric acid esters, liquid aliphatic oil sulfuric acid esters, alkylarylsulfonic acid salts and the like; and nonionic surfactants of such as polyoxyethylene alkyl ethers; polyoxyethylene alkyl esters, polyoxyethylene sorbitan alkyl esters, acetylene alcohol, acetylene glycol and the like and one or more of them may be properly selected and used.

The controlling substance is immobilized at desired positions on the base 11 when or after it is disposed on the base by the microdroplet ejection means. In order to immobilize the controlling substance to the base 11, the controlling substance or the base may be subjected to necessary pretreatment for immobilization. The pretreatment of the controlling substance includes introduction of functional groups for covalent bond formation such as amino, carboxyl, disulfide, epoxy, carbodiimide, maleimide groups and the like, or bonding of chargeable substance such as metals, fine particles of inorganic oxide and cationic or anionic polymers, to the substance 12. Alternatively, it is possible to introduce those that bind on the basis of the biological affinity such as avidin or biotin, an antigen or antibody. The pretreatment of the base also includes introduction of functional groups for covalent bond formation such as amino, carboxyl, disulfide, epoxy, carbodiimide, maleimide groups and the like after coating the base surface with a polymer or a silane coupling agent. Alternatively, an electroconductive or semiconductive layer may be formed on the base surface to charge the surface by applying metal such as gold, silver, platinum, iron and the like; inorganic oxide such as indium tin oxide, titanium oxide, zinc oxide and the like; and further, electrically conductive polymer such as polyacetylene, polypyrrole, polyaniline, polythiophene and the like. Furthermore, materials having binding activity to the pretreated controlling substance by biological affinity such as biotin, avidin, antibodies, antigens, protein A that binds to antibodies may be provided on the surface of the base 11. Introduction of these substances allows firm bonding between the surface of the base 11 and the controlling substance 12.

On immobilization, energy may be applied from outside, for example, by light irradiation or heating. This promotes bonding of the surface of the base 11 and the controlling substance 12.

Substratum 1 can be produced as described above.

Next, the cell culture method using the above-described substratum 1 is described. By culturing cells in a state that the culture fluid is in contact with at least the immobilization area of the substratum 1, cells can be cultured in such a manner that at least one of cell adhesion, proliferation, differentiation, survival, maintenance of undifferentiated state and cell apoptosis is controlled. Cells are not particularly limited, but preferably such cells that the immobilized substance can affect any of the functions described above. If necessary, the substratum 1 can be sterilized by UV irradiation to avoid undesirable microbial contamination. Although cell culture may be carried out by immersing the whole substratum 1 in the culture medium, it is possible to culture cells controlling at least one of the above-described cellular functions if the culture medium is in contact with at least the immobilization area of the controlling substance.

It is also possible to add a desired substance to the culture, during cells are grown on the substratum 1 or after a certain culture period to change the cell proliferation, differentiation or cell adhesion to the substratum. Alternatively, cell culture may be carried out by contacting the flow of the culture medium to the controlling substance, that is, by circulating the culture medium.

Further, during or after a certain period of cell culture on the substratum 1, the cultured cells may be removed from the substratum. This enables repeated use of the substratum or utilization of the removed cells as an artificial tissue or part thereof.

Second Embodiment

Next, a second embodiment according to the invention is described.

The technology of in vitro proliferation and differentiation of stem cells to various functional cells has been considered very important in view of future development of regeneration medical treatment. However, it is very difficult to arrange cells and to control their proliferation or differentiation during cell culture, being a serious obstacle to the research and development of such cell utilization as described above. In Protein, Nucleic acid, Enzyme, 45-5, 727-734, (2000), it is reported that a cell growth factor that affects cell proliferation or differentiation was immobilized with a pattern size of equal to or smaller than a cell by using photolithographic technique, and the effect of the growth factor on proliferation of the cells cultured on the substratum by measuring the amount of produced proteins. In this report, the direction of nerve cell elongation was controlled by a nerve growth factor immobilized by photolithography in a pattern equal to or smaller than the cell in size.

However, production of a culture substratum using a photolithographic method is complicated because it requires repeating steps such as exposure and development. Further, there are problems that biomaterials, for example, those scarcely existing in a living body, may be wasted during the production process.

Further, when a plurality of controlling substances such as cell-adhesive proteins and cell growth factors are immobilized by photolithography in order to control the cell adhesion, proliferation or differentiation, the substance already immobilized and the substances to be immobilized by photolithography will come into contact, which inevitably causes nonspecific adsorption between them. As a result, immobilization of controlling substances at unintended areas would occur. Thus, according to the investigation by the inventors, it is extremely difficult to control the cell adhesion, proliferation, and differentiation as intended.

On the other hand, the inventors have found that the above-described problems can be solved by using microdroplet ejection means as employed in the above first embodiment and cell culture substata that provide highly precise control of cell proliferation and differentiation can be obtained.

That is, according to the second embodiment, the cell culture substratum bears a pattern of the controlling substance formed by microdroplet ejection means on it, where the pattern is of a band or dot shape and its width is equal to or smaller than that of the cell to be cultured.

Here, the term "equal to" means being the same to less than 2 fold, preferably being the same to less than 1.5 fold. In other words, the width of the pattern is preferably smaller than 2 fold of the cell size. By this, only one cell can adhere to the pattern in its width, so that the direction of growth or differentiation of the cell is automatically restricted. As a result, it is possible to control individual cell adhesion, orientation, proliferation and differentiation. More particularly, it is possible to provide tissue-like structure of cells after cell cultivation. FIG. 3 is a schematic illustration of a production method of a cell culture substratum according to this embodiment. In FIG. 3, the reference numeral 31 denotes a base, the reference numeral 13 denotes an ink jet recording head, and the reference numeral 22 denotes a droplet of a liquid containing a controlling substance 12 ejected from the head 13. Application of the droplet to the surface of the base 31 provides a substratum 3 for cell culture. The width (X) of respective isolated areas of the attached controlling substance 12 is preferably such that two or more cells to be cultured cannot attach together on it, and practically the width X is less than two fold of the cell width. Although the size of the cell depends on the cell type, generally it is in an order of micron. Hence, when the substratum is produced by the above-described method, the volume of the droplets ejected from the ink jet recording head is, for example, not larger than 100 pl, preferably not larger than 10 pl, and more preferably not larger than 4 pl. By adjusting the volume of the droplets in such a range, cells can be more precisely controlled during the culture process. Specifically, by employing droplets of 4 pl, dots about 10 to 30 µm in diameter are formed on the base, although it depends on the type and the surface state of the base. A substratum to which the controlling substance is attached in such a size is extremely suitable for controlled cell culture. According to such a method, only a necessary amount of the controlling substance solution is ejected to the base with position control, not wasting the substance as in photolithography method where the substance is applied to an area that will be removed in the following development process. Thus, the substratum production is extremely efficient. As a more preferable embodiment, the controlling substance attached to the base is immobilized by one of the methods described in the first embodiment in detail.

In this embodiment, the same controlling substances and bases as used in the first embodiment can be used, so that explanation is omitted. Further, the substratum according to the second embodiment may have a plurality of different patterns, for example a first pattern and a second pattern on the same substratum. Also, in such a case, the controlling substance may be the same or different between patterns.

Further, the first pattern and the second pattern may respectively contain a plurality of types of controlling substances (for example, a first controlling substance and a second controlling substance). Further, in such a case, the combinations of the first and the second controlling substances contained respectively in the first and the second patterns may be the same or different. Further, when the combinations are the same, the ratios of the first and the second controlling substances in the first pattern and the second pattern may be different. As described above, by adjusting the types of controlling substances contained in a plurality of patterns arranged on the substratum, it may be possible to differentiate and grow cells of different functions on a single substratum.

Figure 4:
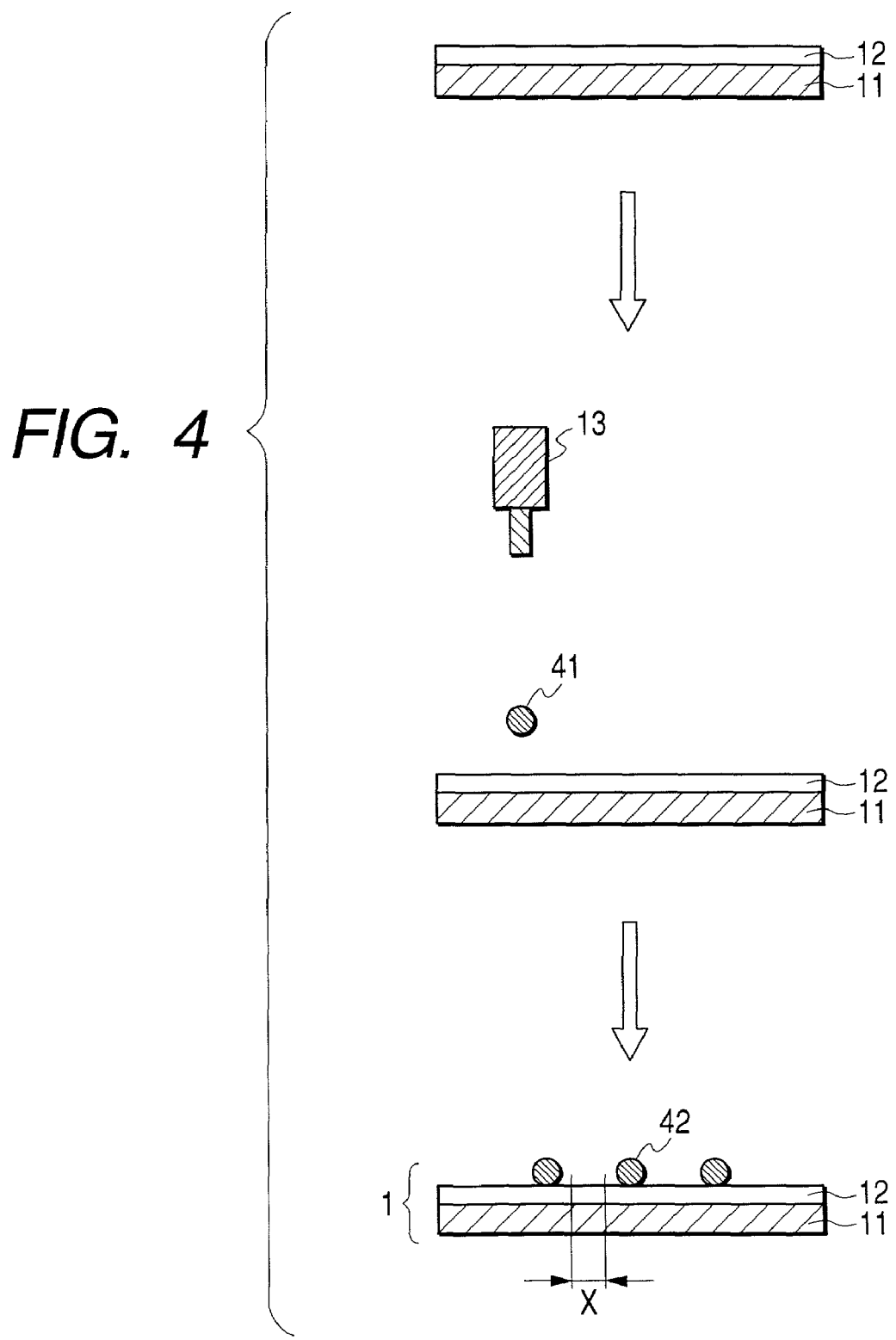
FIG. 4 is a process flow chart of another exemplary production method of a substratum according to the second embodiment.

FIG. 4 is an illustration of another production method of a substratum according to the second embodiment. The substratum is prepared by disposing a substance to which cells cannot adhere (hereinafter referred to as non-adhesive substance) on the surface so as to make the width of a pattern of the controlling substance on the surface equal to or smaller than the width of cells to be cultured. For example, a layer of the controlling substance 12 is formed on the entire surface of the base 11 and then droplets 41 of a solution of a non-adhesive substance are applied by using microdroplet ejection means 13 to dispose the non cell adhesive substance 42 on the layer of the controlling substance 12 in such a manner that the pattern width of the exposed controlling substance 12 is equal to or smaller than that of the cells to be cultured thereon to produce the cell culture substratum according to the second embodiment. This method can cut down consumption of the non-adhesive substance 42. In this embodiment, the non-adhesive substance 42 may be a polymer material or a low molecular weight compound, not restricted to biological substances. Thus, various methods and various materials can be employed allowing easy formation of areas where the controlling substance.

Figure 5:
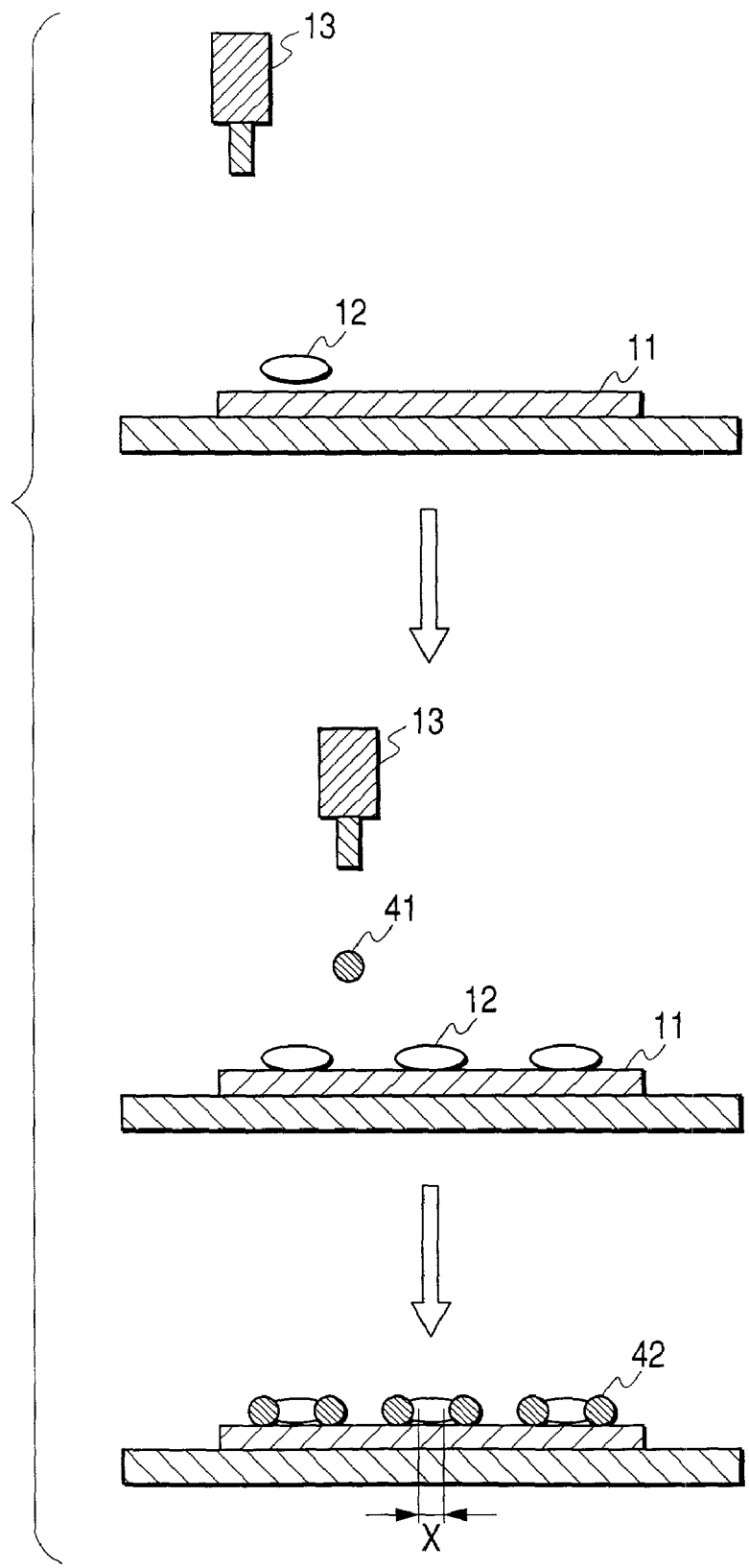
FIG. 5 is a process flow chart of another exemplary production method of a substratum according to the second embodiment.

The method shown in FIG. 4 forms a layer of the controlling substance 12 on the surface of the base 11 beforehand, but it is also possible, as shown in FIG. 5, to apply droplets containing the controlling substance 12 first, and then the droplets 41 containing the non-adhesive substance 42 are applied by using microdroplet ejection means. At this time, the substance 42 is arranged so as to be adjacent to or overlapping the controlling substance area to make the width of the area where the controlling substance is exposed equal to or smaller than that of the cells to be cultured.

Figure 6:
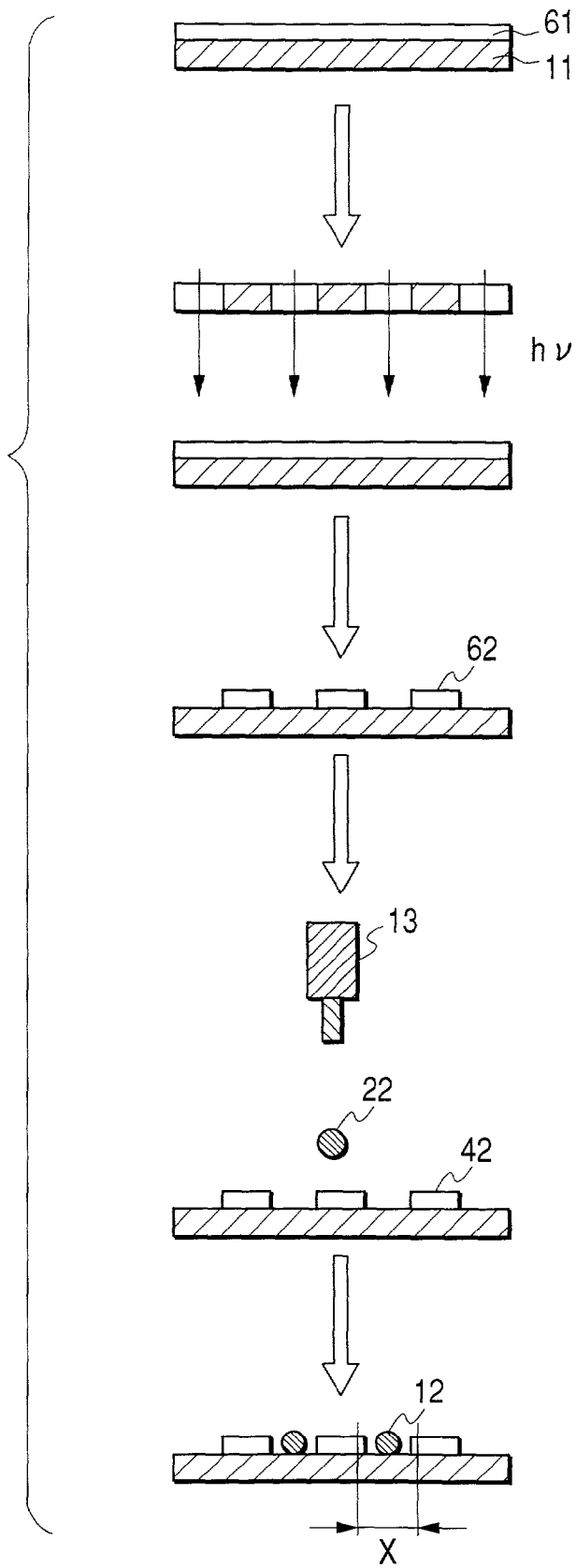
FIG. 6 is a process flow chart of another exemplary production method of a substratum according to the second embodiment of the invention.
Figure 7:
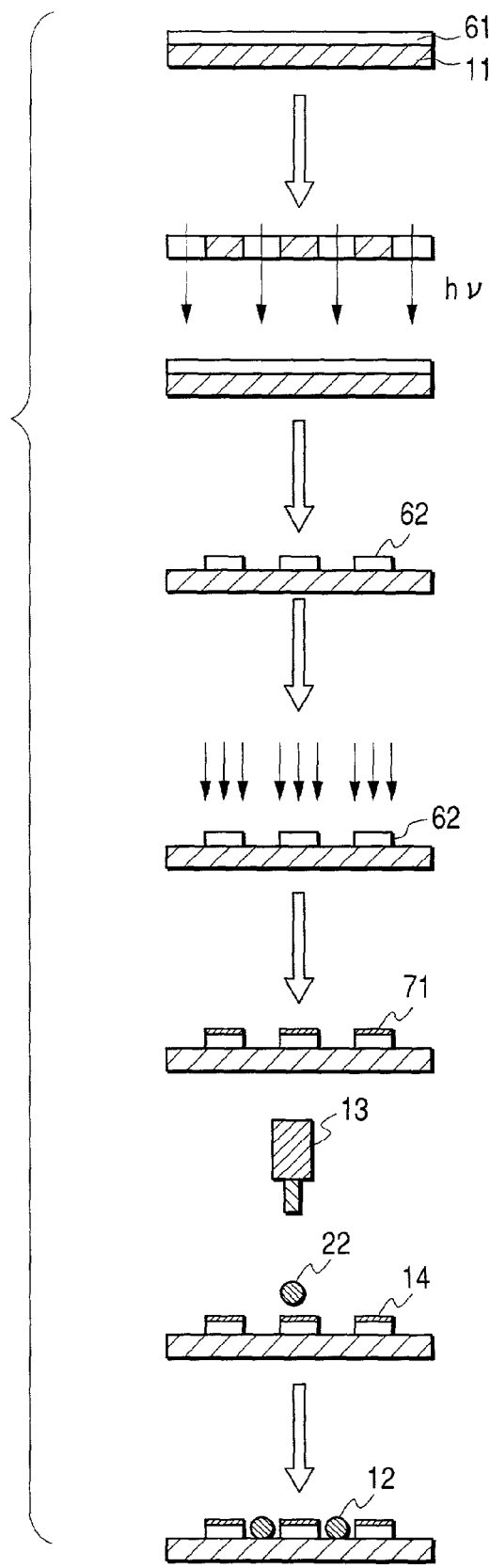
FIG. 7 is a process flow chart of another exemplary production method of a substratum according to the second embodiment.

FIG. 6 is a schematic view illustrating another embodiment of such a cell culture substratum and a production method thereof. This method comprises the step of forming a rising portion 62 of the non-adhesive substance 42 and the step of applying the droplets containing the controlling substance 12 to the area surrounded by the rising portion to dispose the substance 12 thereto. By employing this method, a plurality of patterns of the controlling substance can be formed on a substrate in such a manner that patterns are isolated from one another by the rising portion. Practically, as shown in FIG. 6, for example, a photoresist layer 61 is formed on the base 11 and selectively exposed and developed to form rising portions 62 made of the non-adhesive substance 42 on the base 11 and then the controlling substance 12 is supplied to the areas surrounded by the rising portions 62 by the microdroplet ejection means 13, so that the cell culture substratum 1 according to this embodiment can be obtained. Since the droplets 22 containing the controlling substance 12 are applied to areas that have been restricted by the non-adhesive substance 42, the controlling substance 12 can be disposed with precise size control. Further, the surface of the rising portions 62 may be subjected to water repelling treatment 71, as shown in FIG. 7, before droplets containing the controlling substance 12 are ejected to the base 11. By such a treatment, droplets containing the controlling substance 12 are repelled by the rising portions and disposed in areas surrounded by the rising portions, without running over. Alternatively, if necessary, the non-adhesive substance 42 can be disposed after the controlling substance 12 was disposed on the base 11 by the microdroplet ejection means.

Next, a method for culturing cells using the cell culture substratum according to the second embodiment of the invention is described. When cells are culture on the substratum in which the width of the respective areas of the controlling substance 12 is the same as or smaller than the size of cells to be cultured, the adhesion and orientation of the individual cells can be controlled and also at least one of cell proliferation and differentiation can be controlled. Consequently, the cells proliferate or differentiate while the orientation of the individual cells is controlled, which has not been achieved in tissue culture, and enables production of tissues similar to those in the living body. Cells to be cultured are not particularly limited and any cells can be cultured. If necessary, the substratum 1 can be sterilized by UV irradiation to avoid undesirable microbial contamination. Although cell culture may be carried out by immersing the whole substratum 1 in the culture medium, it is possible to culture cells controlling at least one of the above-described cellular functions if the culture medium is in contact with at least the immobilization area of the controlling substance.

It is also possible to add a desired substance to the culture, during cells are grown on the substratum 1 or after a certain culture period to change the cell proliferation, differentiation or cell adhesion to the substratum. Alternatively, cell culture may be carried out by contacting the flow of the culture medium to the controlling substance, that is, by circulating the culture medium.

Further, during or after a certain period of cell culture on the substratum 1, the cultured cells may be removed from the substratum. This enables repeated use of the substratum or utilization of the removed cells as an artificial tissue or part thereof.

It is possible to construct a cell culture system by combining the above-described substratum production and cell culture using the substratum as a series of steps, i.e., from substratum production to cell culture. In FIG. 9, the reference numeral 901 denotes a storage chamber for a base 11 of the cell culture substratum 1. The base 11 is sterilized there and then transported to a production chamber 902 to produce the cell culture substratum. There, the cell culture substratum bearing the controlling substance on the surface is produced by any method described above referring to FIG. 1 to FIG. 8. Next, the substratum is transported to a culture chamber 903 and cells are cultured as described above. Then, the obtained products of the culture are transported to the chamber 904 and taken out.

Figure 10:
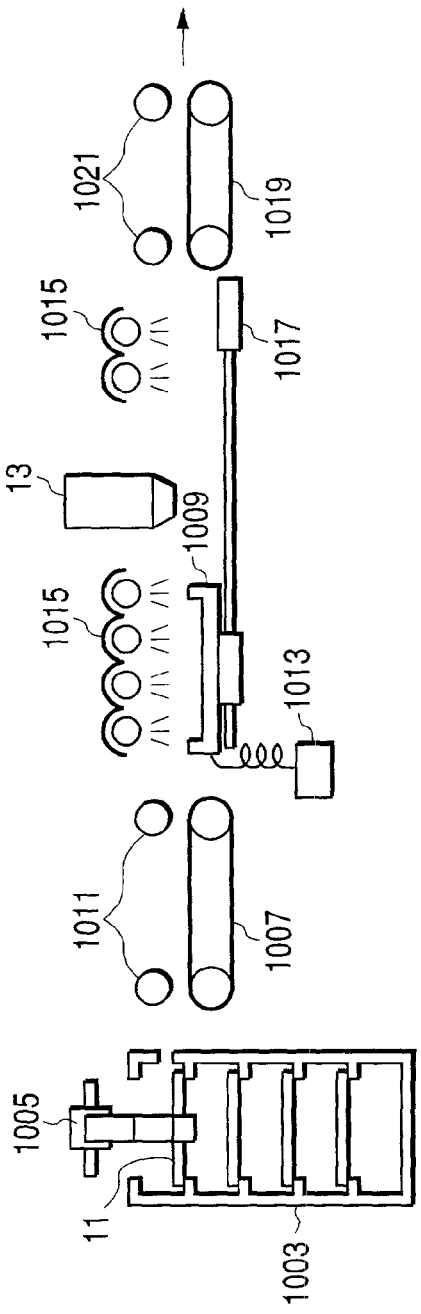
FIG. 10 is a cross-sectional view exemplarily illustrating the inside of the base storage chamber and the substratum production chamber in the cell culture apparatus shown in FIG. 9.

FIG. 10 is a detailed illustration covering from the storage chamber 901 to the substratum production chamber 902. The base 11 is set in a stocker 1003 and fed to a belt conveyer 1007 by a transporting apparatus 1005 and fed to a tray 1009. The reference numeral 1011 denote an auxiliary roll for feeding. The base 11 fed to the tray 1009 is firmly adsorbed and fixed on the tray by suction force by a pump 1013. The base 11 on the tray 1009 is fed to an area where a first treatment step is carried out. The reference numeral 1015 is a $UV/O_3$ lamp to carry out pretreatment of the base 11. When the substrate is transported from the area of the first step by a sending motor 1017, droplets containing the controlling substance are supplied by microdroplet ejection means 13. The base to which the controlling substances were supplied is immediately transported to an area where the third step of immobilization treatment is carried out, in this case, by an UV radiation lamp 1015. The substrate subjected to the above-described three treatment steps is transported to a next culture chamber 903 through a belt conveyer 1019 and feeding rollers 1021.

A cell screening apparatus according to the invention may be a different style other than that described above and is not particularly restricted if the apparatus is capable of achieving the above-described purposes.

First Embodiment

Example 1

Substratum for Promoting Growth of Mouse Fibroblast STO by Insulin

A 0.5% solution of 3-aminopropyltriethoxysilane in ethanol was applied onto a glass base and dried at room temperature for 24 hours.

Separately, N-hydroxysuccinimido group was introduced into insulin by the following method: 1-ethyl-3-(3-dimethylamino)propyl)carbodiimide (WSC) dissolved in deionized water was added dropwise to 60 mmol of N-hydroxysuccinimide dissolved in deionized water and stirred at 4° C. for 24 hours. Successively, the foregoing reaction solution was added dropwise to 60 mmol of insulin dissolved in an isotonic phosphate buffer solution and stirred at 4° C. for 24 hours. Then the reaction product was dialyzed with the isotonic phosphate buffer solution to remove unreacted substances to obtain a solution of N-hydroxysuccinimidized insulin.

Next, an ink cartridge of which is an ink jet printer (BJF 870, manufactured by Canon, a thermal ink jet printer) was fully washed with the isotonic phosphate buffer solution. The dialyzed insulin solution prepared above was diluted to 50 μg/ml with an aqueous solution of 50% ethanol. The diluted insulin solution was loaded in the ink cartridge and disposed onto the base by the ink jet printer. The print pattern was controlled by a personal computer connected to the printer and the size of one droplet was controlled to be about 4 pl. After ejection of the insulin solution, the base was dried at room temperature and then incubated at 35° C. for 1 hour to carry out immobilization reaction of the insulin on the base. After immobilization, the base was washed with the isotonic phosphate buffer solution to remove the unreacted insulin. In such a manner, a substratum for promoting growth by insulin was produced.

On this substratum, mouse fibroblast STO was cultured. As a culture medium, DMEM (Dulbeccos Modified Eagles minimum essential medium) containing 10 μg/ml transferrin was employed. The substratum was put in a glass petri dish and culture was carried out at 37° C. for 24 hours under humid air (95 to 100% RH) with 5% of $CO_2$. The morphology of the cells on the substratum was observed by an optical microscope. As a result, in the areas where insulin was immobilized, dense proliferation of mouse fibroblast STO cells was observed.

Example 2

Substratum Immobilizing Fibronectin and Insulin

In the same manner as in Example 1, a substratum to which fibronectin and insulin were immobilized was produced. Fibronectin was immobilized on the base in the same manner as in Example 1. Insulin was biotinylated using a biotin-labeling kit (Dojin Kagaku Co.). Biotin was also introduced to the base surface using the biotin-labeling kit. Then, avidin was disposed onto the base surface using a piezo-type ink jet printer (PM 900C, Seiko Epson Corp) to immobilize avidin by biological affinity. Then, biotin-labeled insulin was disposed by the ink jet printer PM 900C to immobilized it by reaction with the avidin immobilized on the base. In this case, three types of areas on the base, that is, (i) an area where only fibronectin was immobilized, (ii) an area where only insulin was immobilized, and (iii) an area where fibronectin and insulin, were immobilized. The area (ii) where both fibronectin and insulin were immobilized was formed by controlling the printer to make two kinds of droplets overlap on the base.

Mouse fibroblast STO cells were cultured on the substratum with a culture medium of DMEM at 37° C. for 24 hours in a humid air (95-100% RH) containing 5% $Co_2$. After cultivation, the change of the cell number was measured by staining and counting the cell nuclei. The substratum was taken out of the culture medium, washed with the isotonic phosphate buffer solution, and immersed in methanol for 30 minutes to fix cells on the substratum. Separately, a 10,000 fold dilution of Hoechst 33258 was applied to the substratum and then reacted for 5 minutes. After that, the substratum was washed with the isotonic phosphate buffer solution and observed under a fluorescent microscope to count the number of the stained nuclei. As a result, in the area where both fibronectin and insulin were immobilized, cell growth was active and the cell density was 10,000/mm$^2$. On the other hand, in the area where only insulin was immobilized, no cell was observed, and in the area where only fibronectin was immobilized, cell growth was not so active with a cell density of about 10/mm$^2$.

Example 3

Substratum Having Immobilized Insulin at Various Dot Densities

In the same manner as in Example 1, a substratum on which insulin was immobilized was prepared except that the dot density was changed area by area. To change the density, hatching patterns with different densities of dots were drawn using a drawing software and the drawing data of the patterns were transmitted to the printer from a personal computer to produce patterns with different dot densities according to the position on the substratum. Specifically, areas of 50%, 30, and 10% and 2% dot area per unit surface area were formed respectively.

When mouse fibroblast STO cells were cultured on the substratum by the same culture method as in Example 1, the density of cells increased as the density of insulin increased. When the density of cells was measured by the nucleus staining method as in Example 2, the number of cells was 10,000/mm$^2$ in the 50%-dolt area, 3,000/mm$^2$ in the 30%-dot area, 300/mm$^2$ in the 10%-dot area, and 100/mm$^2$ in the 2%-dot area.

Example 4

Substratum Having Electrostatically Immobilized Insulin

An ITO (indium tin oxide) layer was formed on a base by sputtering. Untreated insulin was disposed on the base by an ink jet printer. With a culture medium similar to one used in Example 1 was kept at pH 7.0 and a voltage was applied between the ITO layer on the base and a platinum electrode as a counter electrode to charge the base surface positive. Since the isoelectric point of insulin is about pH 5.3, insulin was charged negative in the vicinity of pH 7.0 to be immobilized onto the base.

When mouse fibroblast STO cells were cultured on such a substratum, cell proliferation was observed in the areas where insulin was immobilized.

Example 5

Substratum Having Fallen Immobilization Area

A photoresist OFPR-800 (Tokyo Ohka Kogyo Co., Ltd.) was applied to a glass base and a fine resist pattern was formed by a photolithographic process. The base was then immersed in a hydrofluoric acid solution to etch the glass surface where the resist was removed and to form sunken areas on the surface. The wells were patterned not to communicate each other to prevent mixing of the culture medium.

The above-described sunken areas on the base were treated with the silane coupling as in Example 1, and a solution of fibronectin treated to have a linker as in Example 2 was ejected to the wells by an ink jet printer to form an immobilization area of fibronectin in each well.

Using the substratum produced in such a manner, mouse fibroblast STO cells were cultured.

Different culture media, i.e., bovine fetus serum culture medium, DMEM, DMEM supplemented with 10 μg/ml of transferrin and DMEM supplemented with 10 μg/ml of transferrin and 1% insulin, were used for respective areas. As a result, no cell proliferation took place in the DMEM culture and the DMEM with transferrin, whereas cell proliferation was observed in the bovine fetus serum culture medium and the transferrin and 1% insulin-containing culture medium.

Example 6

Substratum Having Areas Surrounded by Wall-Like Structure

To epidermal growth factor (EGF), a functional group was introduced by the following method. A tetrehydrofuran (THF) solution containing 50 mmol dicyclohexylcarbodiimide (DCC) was added dropwise to a THF solution containing 50 mmol N-hydroxysuccinimide and 45 mmol 4-azidobenzenecarboxylic acid and reacted at 4° C. for 24 hours with stirring. After being vacuum-dried, the reaction product was recrystallized from an isopropanol/diisopropanol solution and purified. Successively, the resulting reaction product was dissolved in dimethylformamide and EGF dissolved in an isotonic phosphate buffer solution (pH 7.0) was added dropwise and stirred at 4° C. for 48 hours to introduce azido group into EGF.

Further, a photoresist OFPR-800 (Tokyo Ohka Kogyo Co., Ltd.) was applied to a polysulfone base to form wall-like structure by a photolithographic process.

Successively, to the areas surrounded by the wall-like structure on the base, a solution of the above azido-EGF was ejected by an ink jet printer. After drying, EGF-immobilized areas were formed by irradiating at 200 mJ/cm$^2$ using a UV lamp. Unreacted EGF was washed out by the isotonic phosphate buffer solution to obtain the substratum for cell culture.

On the substratum, PC 12 cells were cultured with the same culture medium as in Example 1. PC 12 cells did not proliferate but differentiated growing dendrites.

Example 7

Method of Culture with Supplement

Using the same substratum as in Example 6, PC 12 cells were cultured in DMEM medium. After 48 hours from starting the culture, EGF was added to an immobilization area 1, nerve growth factor (NGF) to an immobilization area 2, and no addition to an immobilization area 3.

As a result, in the immobilization area 1, PC 12 cells started proliferating, in the immobilization area 2, cells grew dendrites, but in the immobilization area 3, no change took place.

Example 8

Culture Method Having a Step of Cell Removal from Substratum

First, a layer of poly(N-isopropylacrylamide) gel was formed on a polystyrene base by casting. Separately, azido group was introduced to insulin by the method employed in Example 6. Then a solution of the insulin having azido group was ejected and immobilized in the same manner as in Example 1 to obtain a substratum for cell culture. On this substratum, mouse muscle cells C2C12 were cultured in DMEM medium. Along the pattern of immobilized insulin, the C2C12 cells proliferated. After 48 hour-culture, the culture substratum was cooled to 30° C. to decrease the adhesion of the polyacrylamide gel layer to the substratum so that the cell mass came up into the culture medium from the substratum. When the floating cell mass was taken out and pulse potential was applied to the cell mass at both ends, the cell mass contracted.

Further, at 37° C. the acrylamide gel layer was formed on the base from which cultured cells had been released, and when cells were cultured on the regenerated substratum, cell proliferation was observed. It implies that the substratum is reusable.

Second Embodiment

Example 9

Insulin Substratum

As shown in FIG. 2, an insulin substratum, a cell culture substratum 1 was prepared by ejecting insulin, a culture control substance 12, was ejected from an ink jet head 13 onto a polyethylene terephthalate (PET) film 11, by using a thermal ink jet printer (trade name BJF 870; manufactured by Canon).

First, the ink cartridge of the ink jet printer was fully washed with an isotonic phosphate buffer solution (pH 7.0). Separately, an insulin solution in an isotonic phosphate buffer solution (pH 7.0) was with an aqueous 50% ethanol solution to a 50 μg/mL insulin concentration. Then the dilution was charged in the ink cartridge. Using one nozzle of the printer connected to a computer, and using a nozzle check pattern installed in the printer driver, a fine line pattern of insulin was formed on the PET film 11.

In this case, the volume of each droplet ejected by the printer in this case was measured as follows. The weight of the ejected solution was measured by weighing the ink cartridge before and after 1,000,000 dot-ejection. Also, the specific gravity of the ink was measured and the volume per one drop of the ink was calculated to find it was 3.5 pl.

The produced insulin substratum had a thin line pattern of insulin with a width of 10 μm.

Next, the insulin substratum was sterilized using a sterilization lamp, and put in a glass petri dish to culture mouse muscle cells C2C12 on it. As a culture medium, DMEM medium containing 10 μg/ml of transferrin was employed. Mouse muscle cells C2C12 were inoculated and cultured at 37° C. for 24 hours under 5% $CO_2$ humid air (95 to 100% RH). When the cell morphology was observed, cells were proliferating in one line along the thin line pattern of insulin, showing the controlled growth and orientation on the insulin substratum. The width of the cells was 9 μm.

Example 10

Poly L-lysine Substratum

As shown in FIG. 4, an aqueous solution of 1% poly L-lysine, being a controlling substance 12, was applied to a glass base 11 by spin coating to form a 10 nm-thick poly L-lysine coating on the base 11. Poly L-lysine promotes cell adhesion.

Successively, an ink cartridge of a piezoelectric ink jet printer (trade name: PM900C; manufactured by Seiko Epson Corp.) was washed with purified water and charged with a solution containing polyacrylic acid (Table 1). Polyacrylic acid is a non-adhesive substance 42.

TABLE 1

| Content | Composition ratio (wt. %) |
| --- | --- |
| Polyacrylic acid | 5 |
| Purified water | 73 |
| 2-amino-1-methylpropanol | 2 |
| Glycerin | 20 |

Then, the treated glass base was placed on a CD-R print kit (manufactured by Seiko Epson Corp.) and an ink jet printer was connected to a computer to eject the solution in the cartridge from the ink jet head 13 as to form a pattern of polyacrylic acid, using an image drawing software of the computer.

A pattern of polyacrylic acid was formed on the poly L-lysine layer on the base in such a manner that the width of the area where poly L-lysine was exposed was 7 μm or less.

Then mouse DRG cells, a nerve cell, were cultured on the poly L-lysine substratum in a glass petri dish, using the same culture medium as in Example 1 but supplemented with nerve growth factor. Culture was carried out at 37° C. for 48 hours in a humid air (95 to 100% RH) containing 5% of $CO_2$. As a result, DRG cells were growing dendrites along the poly L-lysine area. The size of the cells was 8 μm.

Example 11

Insulin Substratum

Figure 8:
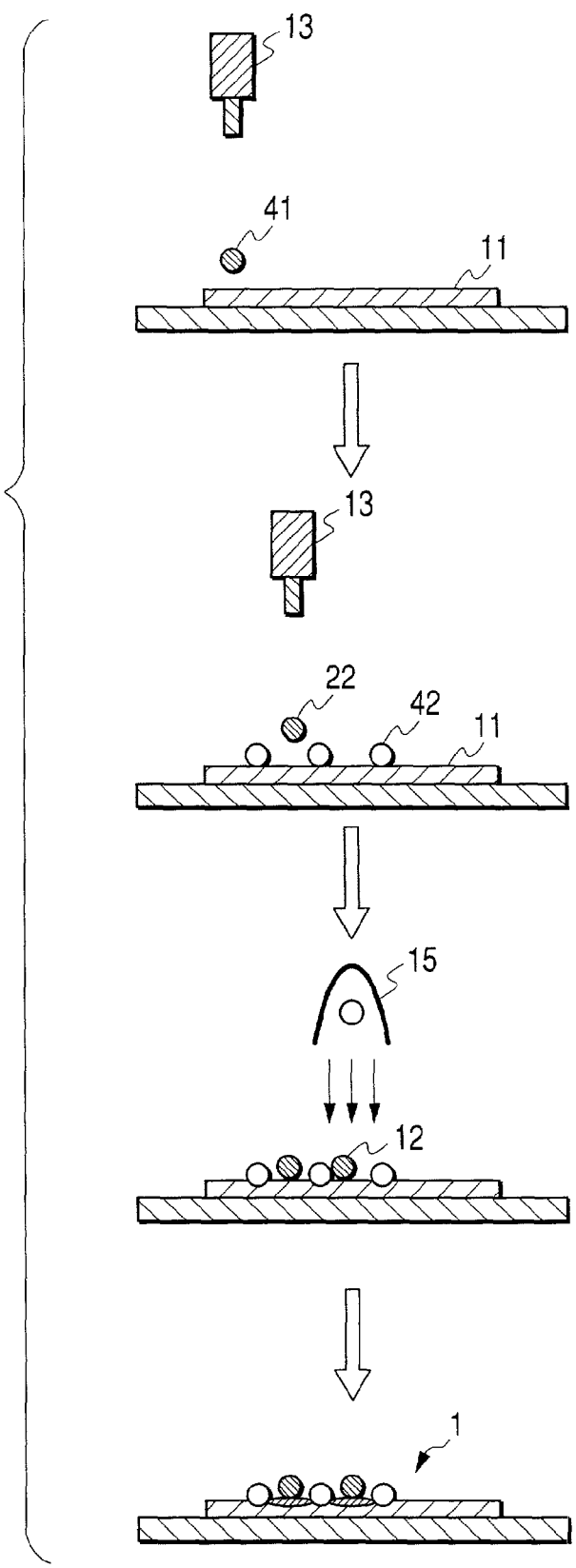
FIG. 8 is a process flow chart of another exemplary production method of a substratum according to the second embodiment.
Figure 9:
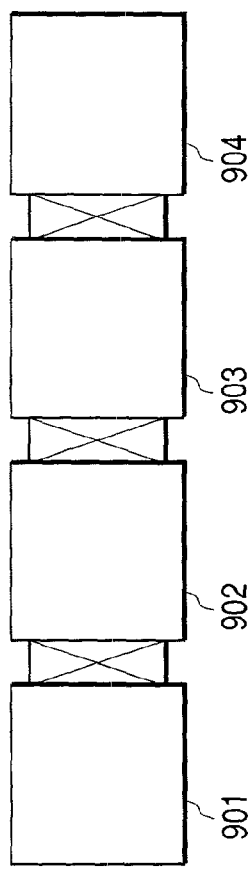
FIG. 9 is a schematic view of a cell culture apparatus according to the invention.

As shown in FIG. 8, a substratum 1 for controlled cell culture was produced by disposing insulin, a controlling substance 12, on a PET film 11. A solution of a water-repellant was prepared by diluting Unidyne TG 991 (produced by Daikin Industries, Ltd.) to 30 wt. % with purified water. Then an ink cartridge of an ink jet printer washed with purified water was charged with the water-repellant solution. The ink cartridge, an ink jet head 13 connected with the cartridge and a control substrate of an ink jet printer were dismounted and arranged in such a manner that droplets are ejected from the nozzle of the head under computer control, and the head can be located at desired positions over the base 11. The PET film was fixed on a stage and placed under the ejection orifice of the head. In such a manner, a pattern of the non-adhesive substance 42 was formed on the PET film.

Successively, in order to immobilize insulin on the base 11, a functional group was introduced to insulin by the following method. A tetrahydrofuran (THF) solution of 50 mmol dicyclohexylcarbodiimide (DCC) was added dropwise to a THF solution containing 50 mmol of N-hydroxysuccinimide and 45 mmol of 4-azidobenzenecarboxylic acid and reacted at 4° C. for 24 hours with stirring. After vacuum-drying, the reaction product was recrystallized in an isopropanol/diisopropanol solution to be refined. Successively, the reaction product was dissolved in dimethylformamide, to which insulin dissolved in an isotonic phosphate buffer solution (pH 7.0) was added dropwise. Reaction was carried out at 4° C. for 48 hours with stirring to introduce azido group to insulin.

A solution of azido-insulin of which composition is shown in Table 2 was charged in an ink cartridge washed with purified water.

TABLE 2

| Content | Composition ratio (wt. %) |
| --- | --- |
| Insulin | 1 |
| Isotonic phosphate buffer solution | 59 |
| Glycerin | 20 |
| Ethylene glycol | 20 |

In the same manner as before, the insulin solution was ejected from the head 13 to the PET film base 11, on which a pattern of non-adhesive substance 42 had been formed. After drying, the base was UV irradiated using an ultraviolet lamp to immobilize the insulin on the PET film.

When the produced substratum was observed, the pattern of insulin was formed in the vicinity of the pattern of the water-repellant. The width of the insulin pattern was 7 μm.

Cell culture on the substratum produced as above were carried out as follows: The insulin substratum was immersed in the same culture medium as used in Example 1, and Chinese hamster ovarian cells (CHO) were inoculated. Culture was carried out at 37° C. for 48 hours in a humid air (95 to 100% RH, 5% $CO_2$). CHO cells proliferated along the insulin pattern in one line. The size of the cells was 8 μm.

Example 12

Interleukin-1-fibronectin Substratum

As shown in FIG. 5, a culture substratum 1 was produced by immobilizing interleukin-1 and fibronectin on a base 11 of PET film.

First, functional groups for immobilization were introduced to both interleukin-1 and fibronectin, control substances 12, by the same method as in Example 11. After that, the interleukin-1 and fibronectin were diluted to 50 μg/ml with an aqueous 50% ethanol solution. Then the dilutions were loaded separately to different ink cartridges previously washed with an isotonic phosphate buffer solution, and ejected to the base 11 from the ink jet heads 13 using an ink jet printer. In FIG. 5, for convenience, the same reference numeral is assigned to interleukin-1 and fibronectin, culture control substance 12. After drying, ultraviolet rays were radiated to the base 11 in the same manner as in Example 11 to immobilize interleukin-1 and fibronectin. Next, the same solution of polyacrylic acid (non-adhesive substance 42) as employed in Example 10 was charged into an ink cartridge of the ink jet printer, and ejected onto the base 11 to make the width of the exposed area of interleukin-1 and fibronectin 8 μm. As described above, an interleukin-1 and fibronectin substratum 1 was produced, where the polyacrylic acid coating was formed so as to partly cover the areas where interleukin-1 and fibronectin were immobilized.

Cell culture on the culture substratum 1 was carried out as follows. The produced interleukin-1-fibronectin substratum was immersed in the same culture medium as used in Example 9 in a glass petri dish and mouse vascular endothelial cells were inoculated to it. Culture was carried out at 37° C. for 48 hours in a humid air (95 to 100% RH, 5% of $CO_2$ and the mouse endothelial cells proliferated along the interleukin-1-fibronectin pattern in one line. The size of the cells was 8 μm.

Example 13

Substratum Having Areas Surrounded By Wall-like Structure (1)

As shown in FIG. 6, a substratum 1 for controlled cell culture was produced.

First, the functional group was introduced into EGF (epidermal growth factor) by the same method as described in Example 6.

Then, photoresist OFPR-800 (Tokyo Ohka Kogyo Co., Ltd.) was applied to a base 11 made of polysulfone to form wall-like structures made of a non-adhesive substance 42 by photolithography. In this case, the height of the wall-like structures was adjusted to 1 μm and the width of the area surrounded by the wall-like structure was adjusted to 10 μm.

Then, to each area surrounded by the wall-like structure on the base 11, a solution containing EGF into which azido group had been introduced was ejected from an ink jet head 13 using an ink jet printer. After drying, the base was irradiated with ultraviolet rays at 200 $mJ/cm^2$ using an ultraviolet radiation lamp. The unreacted EGF was washed out with an isotonic phosphate buffer solution to obtain substratum 1 for controlled cell culture.

PC 12 cells were cultured on the substratum 1 for cell culture. The same culture medium as used in Example 9 was employed. When culture was carried out on the substratum 1, PC 12 cells did not proliferate but differentiated growing dendrites along the pattern.

Example 14

Substratum Having Area Surrounded by Wall-Like Structure (2)

As shown in FIG. 7, a substratum 1 for controlled cell culture was produced.

The functional group was introduced into EGF in the same method as described in Example 6.

Next, wall-like structures made of a non-adhesive substance 14 were formed on a polysulfone base 11 in the same manner as in Example 13. Then, the base was put in a reaction vessel, the pressure of the vessel was adjusted to 10 mPa by a vacuum pump, and a fluoro hydrocarbon gas was introduced to the vessel to carry out water-repelling treatment of the surface of the wall-like structures.

Then, the azido-EGF solution prepared above was ejected to each area surrounded by the wall-like structure on the base 11 using an ink jet printer. After drying, ultraviolet rays of 200 $mJ/cm^2$ were radiated using an ultraviolet radiation lamp. The unreacted EGF was washed out with an isotonic phosphate buffer solution to obtain the substratum 1 for controlled cell culture.

In this example, due to the water-repelling treatment, the droplets ejected by the ink jet printer were disposed without fail in the areas surrounded by wall-like structures.

PC 12 cells were cultured on the substratum 1 for controlled cell culture. The same culture medium as used in Example 1 was employed. When culture was carried out on the substratum 1, PC 12 cells did not proliferate but differentiated growing dendrites along the pattern.

Example 15

Method of Culture with Supplement

Using the same substratum as that of Example 10, PC 12 cells were cultured in the same culture medium as that of Example 9 in two glass petri dishes. After 48 hours from starting the culture, a nerve growth factor (NGF) was added to the culture medium in one glass petri dish A and an EGF was added to the culture medium in the other petri dish B.

As a result, cells in the petri dish B were growing dendrites along the pattern, whereas cells in the petri dish A were proliferating along the pattern.

Example 16

Culture Method Having a Step of Cell Removal from Substratum

A layer of poly(N-isopropylacrylamide) gel was formed on a polystyrene base by casting. On the base, insulin having azido group was immobilized in the same manner as described in Example 11 to obtain a substratum for cell culture. On the obtained substratum, mouse muscle cells C2C12 were cultured in the same culture medium as that of Example 9. Along the immobilized insulin pattern, the C2C12 cells proliferated. After 48 hour-culture, the culture substratum was cooled to 30° C. to decrease the adhesion of the polyacrylamide gel layer to the substratum and the cell mass aligned in one line came up from the substratum in the culture medium. When the cell mass was taken out from the medium and a potential was applied to the both ends of the cell mass, the cell mass contracted.

Further, when cell culture was performed again on the substratum from which cultured cells had been removed once, similar cell mass was formed on it.

According to the present invention, a culture controlling substance can be immobilized at desired positions on a culture substratum by simple steps, which enables culturing cells on the substratum controlling at least one of cell adhesion, proliferation, and differentiation.

Further, according to a cell culture method of the invention, a variety of cells can be cultured on one substratum and cells can be cultured with various substances on one substratum.

Further, a substratum for controlled cell culture according to the invention allows cell proliferation and/or differentiation controlling adhesion and orientation of the cells by culture control substances arranged on the base, thus it enables cell culture under environments similar to in vivo, and is especially useful for in vitro production of tissues having functions almost equal to those in a living body.

Furthermore, since the immobilized culture-controlling substances on a base can stimulate cells continuously, cell proliferation and differentiation can be promoted so as to form a cell constitution having a similar structure as the tissues in the living body on a substratum.

What is claimed is:

1. A substratum having a pattern of a cell-culture controlling substance on a base, said substratum prepared by a process comprising:
   a step of applying a droplet of a first liquid, the first liquid containing a first cell-culture controlling substance, onto a surface of the base;
   a step of applying a droplet of a second liquid, the second liquid containing a second cell-culture controlling substance, onto the base surface so as to overlap the droplet of the first liquid; and
   a step of immobilizing the first and second cell-culture controlling substances on the base,
   wherein the first and second cell-culture controlling substances are able to control at least one function selected from the group consisting of proliferation, differentiation, survival, maintenance of undifferentiated state and apoptosis of cells, one of the first and second cell-culture controlling substances being a cytokine, and
   wherein a region where the first and second cell-culture controlling substances are immobilized has a width of less than two-fold the width of a cell to be cultured on the substratum.

2. The substratum according to claim 1, wherein the first and second cell-culture controlling substances are able to control at least one function selected from proliferation and differentiation of cells.

3. The substratum according to claim 1, wherein the cytokine is a growth factor or a hormone.

4. The substratum according to claim 3, wherein the cytokine is a nerve growth factor, an epidermal growth factor, or a fibroblast growth factor.

5. The substratum according to claim 3, wherein the cytokine is insulin or adrenaline.

6. The substratum according to claim 1, wherein at least one of the first and second cell-culture controlling substances is immobilized to the base by a covalent bond.

7. The substratum according to claim 1, wherein at least one of the first and second cell-culture controlling substances is immobilized to the base by electrostatic bond.

8. The substratum according to claim 1, wherein at least one of the first and second cell-culture controlling substances is immobilized to the base with biological affinity.

9. An apparatus for cell culture, wherein the apparatus comprises means for culturing cells in a state where the first and second cell-culture controlling substances contained by the substratum of claim 1, is brought into contact with a culture medium.

10. The apparatus according to claim 9, wherein the apparatus further comprises means for producing the substratum.

11. The apparatus according to claim 10, wherein the means for producing the substratum comprises a container holding a base, and an apparatus that ejects the first and second liquids.

12. A process for producing a substratum having a pattern of a cell-culture controlling substance on a base, comprising:
   a step of applying a droplet of a first liquid, the first liquid containing a first cell-culture controlling substance, onto a surface of the base;
   a step of applying a droplet of a second liquid, the second liquid containing a second cell-culture controlling substance, onto the base surface so as to overlap the droplet of the first liquid; and
   a step of immobilizing the first and second cell-culture controlling substances on the base, wherein the first and second cell-culture controlling substances are able to control at least one function selected from the group consisting of proliferation, differentiation, survival, maintenance of undifferentiated state and apoptosis of cells, one of the first and second cell-culture controlling substances being a cytokine, and wherein a region where the first and second cell-culture controlling substances are immobilized has a width of less than two-fold the width of a cell to be cultured on the substratum.

* * * * *